(12) United States Patent
Arai et al.

(10) Patent No.: US 11,337,672 B2
(45) Date of Patent: May 24, 2022

(54) INFORMATION PROCESSING APPARATUS, LEARNING DEVICE, AND PROGRAM

(71) Applicant: FUJIFILM Corporation, Tokyo (JP)

(72) Inventors: Takahisa Arai, Kanagawa (JP); Takeyasu Kobayashi, Kanagawa (JP); Shunsuke Kodaira, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 281 days.

(21) Appl. No.: 16/817,569

(22) Filed: Mar. 12, 2020

(65) Prior Publication Data

US 2020/0289081 A1    Sep. 17, 2020

(30) Foreign Application Priority Data

Mar. 14, 2019  (JP) .............................. JP2019-047651

(51) Int. Cl.

| | | |
|---|---|---|
| *A61B 6/00* | (2006.01) | |
| *G06N 20/00* | (2019.01) | |
| *G06N 7/00* | (2006.01) | |
| *G16H 30/20* | (2018.01) | |
| *G01T 7/00* | (2006.01) | |

(52) U.S. Cl.
CPC .............. *A61B 6/586* (2013.01); *A61B 6/582* (2013.01); *G01T 7/005* (2013.01); *G06N 7/005* (2013.01); *G06N 20/00* (2019.01); *G16H 30/20* (2018.01); *A61B 6/502* (2013.01)

(58) Field of Classification Search
CPC ....... A61B 6/4233; A61B 6/502; A61B 6/582; A61B 6/586; G01T 7/005; G06N 7/005; G06N 20/00; G16H 30/20; G16H 40/40; G16H 40/63
See application file for complete search history.

(56) References Cited

U.S. PATENT DOCUMENTS

| | | |
|---|---|---|
| 2011/0073769 A1 | 3/2011 | Enomoto |
| 2017/0188443 A1 | 6/2017 | Nakahara et al. |
| 2018/0253624 A1 | 9/2018 | Schafer et al. |

FOREIGN PATENT DOCUMENTS

| | | |
|---|---|---|
| JP | H08320296 | 12/1996 |
| JP | H11183628 | 7/1999 |
| JP | 2011072417 | 4/2011 |

OTHER PUBLICATIONS

"Search Report of Europe Counterpart Application", dated Aug. 13, 2020, p. 1-p. 5.
Office Action of Japan Counterpart Application, with English translation thereof, dated Dec. 21, 2021, pp. 1-6.

*Primary Examiner* — Mark R Gaworecki
(74) *Attorney, Agent, or Firm* — JCIPRNET

(57) ABSTRACT

A console includes an image processing unit, a defective pixel map data acquisition unit, a failure condition estimation unit, a notification unit, and a display unit. The defective pixel map data acquisition unit acquires defective pixel map data output from a radiography unit. The failure condition estimation unit receives the defective pixel map data acquired by the defective pixel map data acquisition unit and estimates the failure probability of the radiography unit or the usage state of the radiography unit at the time of failure.

10 Claims, 5 Drawing Sheets

INFORMATION PROCESSING APPARATUS, LEARNING DEVICE, AND PROGRAM

CROSS-REFERENCE TO RELATED APPLICATIONS

This application claims priority under 35 U.S.C. § 119(a) to Japanese Patent Application No. 2019-047651 filed on 14 Mar. 2019. The above application is hereby expressly incorporated by reference, in its entirety, into the present application.

BACKGROUND OF THE INVENTION

1. Field of the Invention

The present invention relates to an information processing apparatus, a learning device, and a program that use a radiographic image captured using radiation such as X-rays.

2. Description of the Related Art

In the related art, a radiography apparatus, such as a mammography apparatus, that captures an image of a subject using radiation has been known. The radiography apparatus comprises a radiography unit such as a flat panel detector (FPD). The FPD has an imaging region in which a plurality of pixels that accumulate signal charge corresponding to the amount of incident radiation are arranged.

There is a pixel (defective pixel) that is defective among the pixels forming the FPD. It is difficult for the defective pixel to obtain appropriate signal charge. Therefore, it is necessary to correct the defective pixel. The defective pixel correction is performed by detecting the positional information of a defective pixel of the FPD and correcting the defective pixel using the image data of pixels around the defective pixel in a case in which a radiographic image is displayed.

JP2011-072417A (corresponding to US2011/0073769A1) discloses a method that predicts the lifetime of a radiography unit using an FPD from the positional information of a defective pixel. Specifically, first, the size (the number of pixels) of the pixel defect is calculated and registered in a defect information table. Then, the change characteristics (for example, a linear equation) of a pixel defect are calculated by an operation from the defect information table which has been registered in time series and the time when the pixel defect reaches the upper limit (the size of the pixel defect at which the radiography unit needs to be replaced) is calculated as the lifetime on the basis of the change characteristics. In addition, for the size of the pixel defect calculated in JP2011-072417A, in a case in which a defective pixel (primitive defective pixel) corresponding to one pixel occurs, the size of the pixel defect is 1. As time passes, pixels adjacent to the primitive defective pixel become the defective pixels and the number of defective pixels is added. The added value is recognized as the size of the pixel defect.

SUMMARY OF THE INVENTION

However, the actual deterioration of the radiography unit changes due to not only one parameter, such as the size of the pixel defect, but also several factors, such as the density of defective pixels and the number of defective pixels. In contrast, in JP2011-072417A, in the prediction of the lifetime of the radiography apparatus, the change characteristics of the pixel defect are only calculated from the size of the pixel defect registered in time series. Therefore, in the method disclosed in JP2011-072417A, it is difficult to predict the failure of the radiography unit with high accuracy.

An object of the invention is to provide an information processing apparatus, a learning device, and a program that can predict the failure of a radiography unit with high accuracy.

An information processing apparatus according to the invention comprises a defective pixel map data acquisition unit and a failure condition estimation unit. The defective pixel map data acquisition unit acquires defective pixel map data indicating positional information of a defective pixel which is defective among a plurality of pixels forming a radiography unit. The failure condition estimation unit estimates a failure probability of the radiography unit or a usage state of the radiography unit at the time of failure, using a learned model that receives the defective pixel map data and outputs the failure probability of the radiography unit or the usage state of the radiography unit at the time of failure.

Preferably, the information processing apparatus further comprises a notification unit that sets a threshold value corresponding to the failure probability or the usage state at the time of failure estimated by the failure condition estimation unit and performs notification in a case in which the failure probability or the usage state at the time of failure is greater than the threshold value.

Preferably, the defective pixel map data acquisition unit acquires a calibration image output from the radiography unit as the defective pixel map data.

Preferably, the failure probability is a probability that the radiography unit will be out of order within a preset time.

Preferably, the usage state at the time of failure is a time until the radiography unit is out of order, the number of images captured until the radiography unit is out of order, or the number of times a high voltage is applied to the radiography unit until the radiography unit is out of order.

A learning device according to the invention comprises a learning data acquisition unit, a learning unit, and an evaluation function update unit. The learning unit uses an evaluation function updated by the evaluation function update unit. The learning data acquisition unit acquires learning data in which defective pixel map data indicating positional information of a defective pixel which is defective among a plurality of pixels forming a radiography unit is associated with a recording value of a failure probability of the radiography unit or a usage state of the radiography unit at the time of failure. The learning unit calculates an evaluation value of the failure probability or the usage state at the time of failure from the defective pixel map data using an evaluation function. The evaluation function update unit updates the evaluation function, using an error between the evaluation value of the failure probability or the usage state at the time of failure calculated by the learning unit using the evaluation function and the recording value of the failure probability or the usage state at the time of failure in the learning data, in a case in which the learning data is acquired.

Preferably, the failure probability is a probability that the radiography unit will be out of order within a preset time.

Preferably, the usage state at the time of failure is the number of images captured until the radiography unit is out of order after the use of the radiography unit starts or the number of times a high voltage is applied to the radiography unit until the radiography unit is out of order.

In the learning data, any one of the number of images captured until the radiography unit is out of order after the defective pixel map data is acquired, a time until the radiography unit is out of order after the defective pixel map data is acquired, or an imaging frequency of the radiography unit per predetermined time, the defective pixel map data, and the recording value of the failure probability of the radiography unit or the usage state of the radiography unit at the time of failure are associated with each other.

A program according to the invention drives an information processing apparatus comprising a defective pixel map data acquisition unit that acquires defective pixel map data indicating positional information of a defective pixel which is defective among a plurality of pixels forming a radiography unit. The program causes the information processing apparatus to perform: estimating a failure probability of the radiography unit or a usage state of the radiography unit at the time of failure, using a learned model that receives the defective pixel map data and outputs the failure probability of the radiography unit or the usage state of the radiography unit at the time of failure.

According to the invention, it is possible to predict the failure of a radiography unit with high accuracy.

DESCRIPTION OF THE PREFERRED EMBODIMENTS

Figure 1:
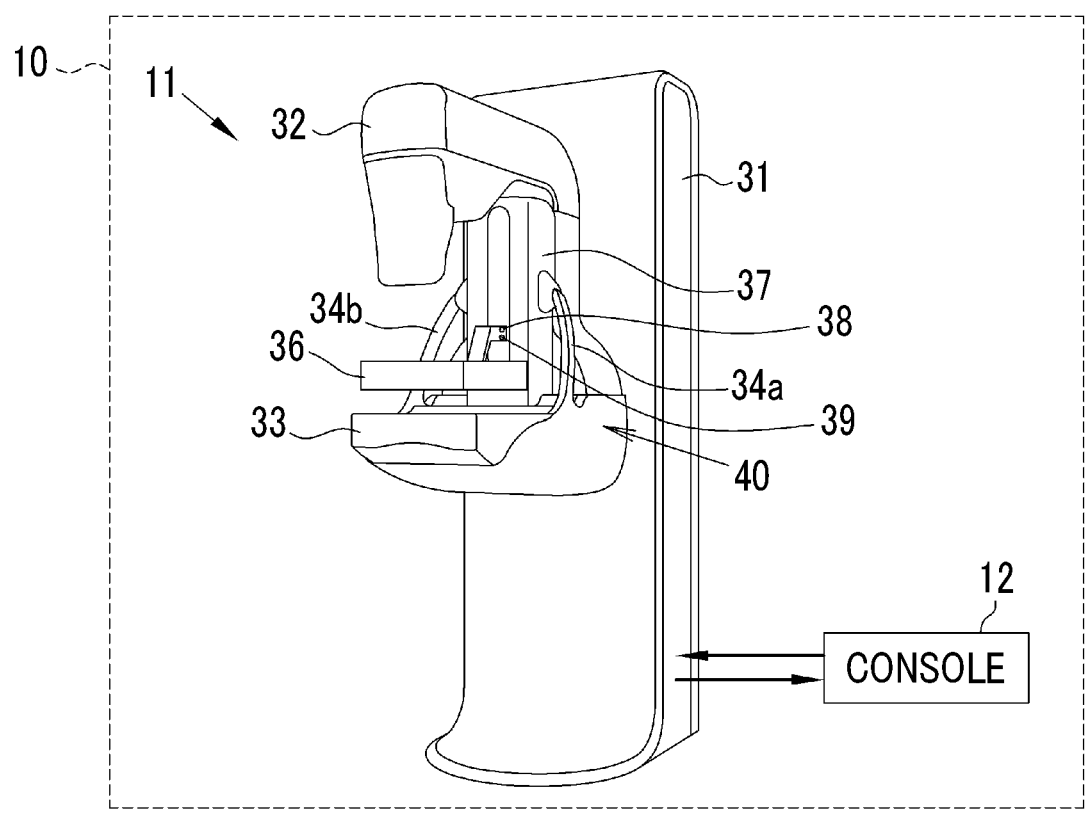
FIG. 1 is an explanation diagram illustrating the configuration of a mammography apparatus.

As illustrated in FIG. 1, a mammography apparatus 10 which is an example of a radiography apparatus comprises an apparatus main body 11 that captures an image of the breast of a subject using X-rays which are radiation and a console 12 that controls the apparatus main body 11. The apparatus main body 11 and the console 12 are connected wirelessly or in a wired manner and transmit and receive data and control signals therebetween if necessary.

The apparatus main body 11 comprises, for example, a support 31, an X-ray generation unit 32, an imaging table 33, a compression plate 36, and an elevating unit 37. The X-ray generation unit 32 and the imaging table 33 are integrated to form a movable unit 40 whose position is adjusted according to the subject in the apparatus main body 11.

The X-ray generation unit 32 includes at least an X-ray tube that generates X-rays. Therefore, in the mammography apparatus 10, the X-ray generation unit 32 is a radiation generation unit that generates radiation (X-rays). In addition, the X-ray generation unit 32 may include a high voltage circuit that supplies a high voltage for generating X-rays to an X-ray tube. That is, the X-ray generation unit 32 may be configured by a so-called mono-tank.

The imaging table 33 is a stage on which the breast is placed and the breast is interposed between the imaging table 33 and the compression plate 36 during imaging. In addition, the imaging table 33 forms a radiography unit that captures the image of the breast of the subject using radiation (X-rays). For example, the imaging table 33 includes, as the radiography unit, an FPD 41 (see FIG. 3) that captures the image of the breast using radiation and a grid that removes scattered radiation (a stationary Lysholm Blende or a mobile Bucky Blende). Further, the mammography apparatus 10 may have a plurality of kinds of grids that can be replaced according to imaging conditions and may perform imaging using the grids. A gripping portion 34a that is gripped by the right hand of the subject and a gripping portion 34b that is gripped by the left hand of the subject are attached to the imaging table 33. The gripping portion 34a and the gripping portion 34b are so-called armrests. Since X-rays are used in this embodiment, the radiography unit is specifically an X-ray imaging unit.

The compression plate 36 compresses and flattens the breast of the subject placed on the imaging table 33 during imaging. This is to reduce the overlap of the normal mammary glands and to easily find the candidates of a lesion such as calcification. The elevating unit 37 moves up and down the compression plate 36 with respect to the imaging table 33. Thus, the elevating unit 37 supports the compression plate 36 substantially in parallel to the imaging table 33 at a specific distance corresponding to the thickness of the breast.

The movable unit 40 is rotatable in a predetermined angle range while maintaining the relative position and direction of the X-ray generation unit 32 and the imaging table 33. Therefore, the apparatus main body 11 can perform imaging in a state in which the imaging table 33 is horizontally disposed or the imaging table 33 is disposed obliquely with respect to the horizontal direction. Specifically, the apparatus main body 11 can perform craniocaudal imaging (CC imaging) in which the imaging table 33 is horizontally disposed and the image of the breast is captured in a craniocaudal direction. Further, the apparatus main body 11 can perform mediolateral oblique imaging (MLO imaging) in which the imaging table 33 is obliquely disposed and the image of the breast is captured in a mediolateral oblique direction.

In the movable unit 40, the X-ray generation unit 32 is rotatable in a predetermined range while the position of the imaging table 33 and the compression plate 36 is fixed. Therefore, the apparatus main body 11 can perform so-called stereo imaging and tomosynthesis imaging. The stereo imaging is an imaging aspect that captures the image of the breast of the subject, which is fixed at a specific position and in a specific direction (for example, the position and direction in the CC imaging), from one direction or a plurality of oblique directions with different inclination angles to obtain a perspective image (hereinafter, referred to as a stereo image) from the oblique direction. In addition, the tomosynthesis imaging is an imaging aspect that captures the images of the breast of the subject, which is fixed at a specific position and in a specific direction, from a plurality of oblique directions and obtains a tomographic image (hereinafter, referred to as a tomosynthesis image) of the breast of the subject using the captured images.

Figure 2:
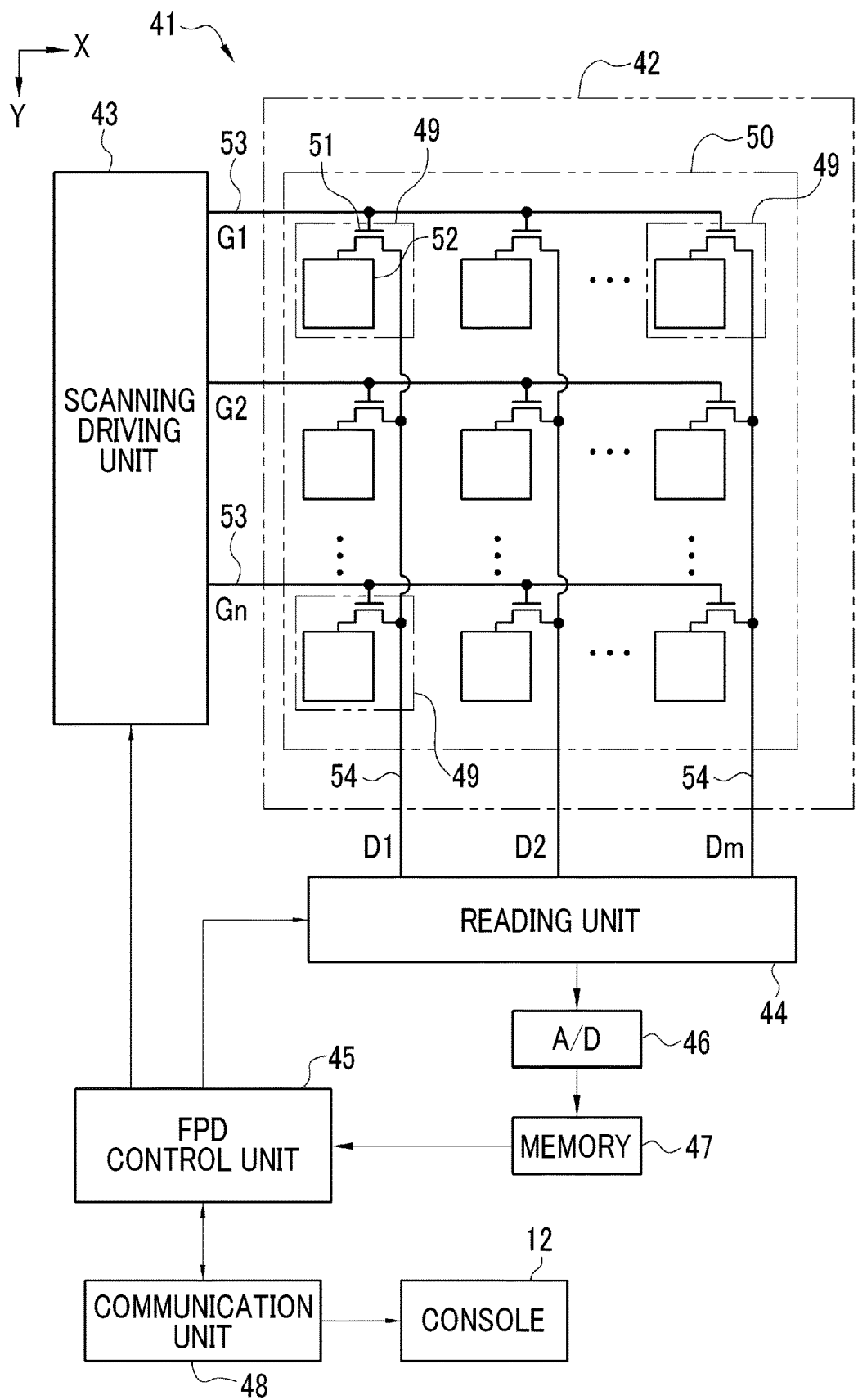
FIG. 2 is a block diagram illustrating the configuration of a radiography unit.

As illustrated in FIG. 2, the FPD 41 as the X-ray imaging unit comprises a conversion panel 42, a scanning driving unit 43, a reading unit 44, an FPD control unit 45, an analog/digital (A/D) converter 46, a memory 47, and a communication unit 48. The conversion panel 42 has an imaging region 50 in which a plurality of pixels 49 that accumulate signal charge corresponding to the amount of incident X-rays are two-dimensionally arranged. For example, the plurality of pixels 49 are arranged at a predetermined pitch in a matrix of G1 to Gn rows (X direction) and D1 to Dm columns (Y direction). The two-dimensional array of the pixels may be a square array as in this embodiment or may be a honeycomb array.

The conversion panel 42 is, for example, a direct conversion type that directly converts X-rays into charge and accumulates signal charge (a first example of an electric signal). In the conversion panel 42, for example, amorphous selenium is used as an X-ray conversion film. In the conversion panel 42, a thin film transistor (TFT) 51, a capacitor (not illustrated) for accumulating signal charge, and a pixel electrode 52 for defining a pixel 49 are formed on an insulating substrate such as a glass substrate. Then, the X-ray conversion film is formed on the TFT 51 and the pixel electrode 52 in the entire surface of the imaging region 50 and a common electrode is formed on the X-ray conversion film. In a case in which X-rays are incident on the imaging region 50, the X-rays are converted into charge by the X-ray conversion film and signal charge is accumulated in each pixel 49 through the pixel electrode 52.

The signal charge accumulated in the pixel 49 is read by the TFT 51. The TFT 51 has a gate electrode connected to a scanning line 53, a source electrode connected to a signal line 54, and a drain electrode connected to the capacitor of the pixel 49. The scanning lines 53 and the signal lines 54 are arranged in a lattice shape. The number of scanning lines 53 provided is equal to the number of rows (n rows) of the pixels 49 and the number of signal lines 54 provided is equal to the number of columns (m columns) of the pixels 49 in the imaging region 50. The scanning line 53 is connected to the scanning driving unit 43 and the signal line 54 is connected to the reading unit 44.

The reading unit 44 includes an integration amplifier that converts the signal charge read from the conversion panel 42 into a voltage signal and a multiplexer that sequentially switches the columns of the pixels 49 in the imaging region 50 and sequentially outputs the voltage signals corresponding to each column.

The reading unit 44 outputs the read voltage signal as an image signal to the A/D converter 46. The A/D converter 46 converts the image signal into digital data and writes the digital data into the memory 47 so as to be associated with coordinates indicating the position of the pixel 49 in the imaging region 50. The FPD control unit 45 transmits the digital image signal in the memory 47 as an X-ray image to the console 12 through the wireless or wired communication unit 48.

The mammography apparatus 10 performs defect correction calibration in addition to the capture of a general X-ray image. The defect correction calibration is calibration accompanied by X-ray irradiation. The defect correction calibration is a calibration for acquiring defect correction data 61A and defective pixel map data which will be described below and is performed during periodic maintenance, in addition to during product shipment and installation. This is because the number of defective pixels change over time.

For example, the periodic maintenance is performed once a day on the day when X-ray imaging is performed using the mammography apparatus 10. In the defect correction calibration, during the periodic maintenance, imaging is performed in a state in which the movable unit 40 is set to the direction and position corresponding to all types of imaging performed by the mammography apparatus 10, such as CC imaging and MLO imaging, to acquire a calibration image.

The calibration image is an image acquired during defect correction calibration involving X-ray irradiation. In a case in which the imaging region 50 is irradiated with X-rays in a state in which the subject does not exist in an irradiation path, the calibration image is generated by the FPD control unit 45 on the basis of the image signal output from the conversion panel 42. Since there is no subject, the entire surface of the imaging region 50 of the conversion panel 42 is uniformly irradiated with X-rays. Therefore, the sensitivity characteristics of each pixel 49 or the information of a defective pixel is reflected in the calibration image. Similarly to the general X-ray image, the FPD control unit 45 transmits an image signal of the calibration image written into the memory 47 to the console 12 through the communication unit 48.

Figure 3A:
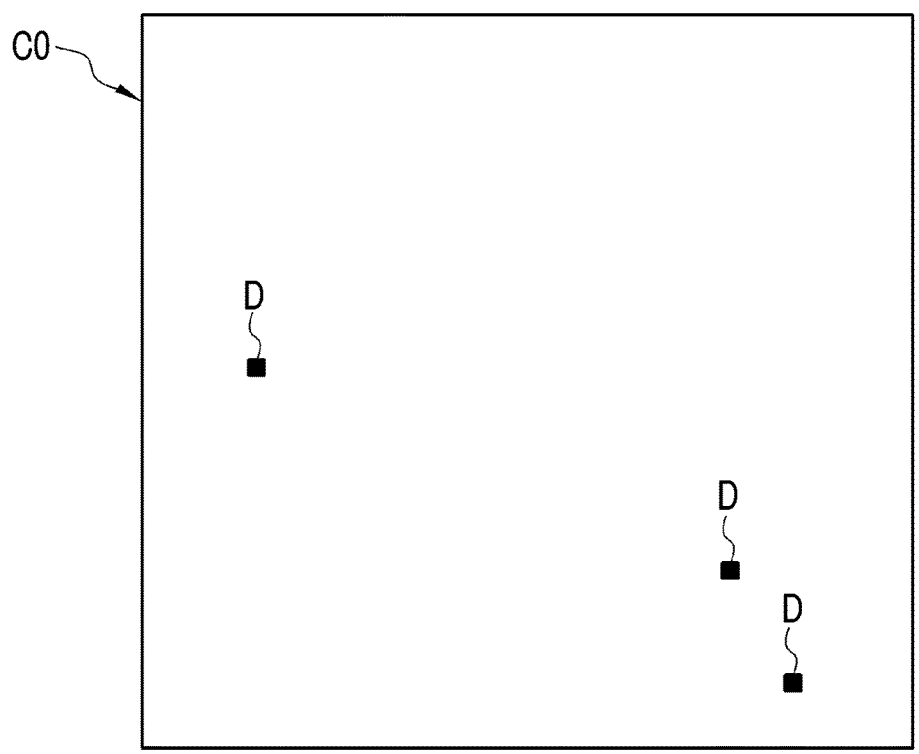
FIG. 3A is an explanation diagram illustrating defective pixel map data in a non-failure state and FIG. 3B is an explanation diagram illustrating defective pixel map data in failure state.
Figure 3B:
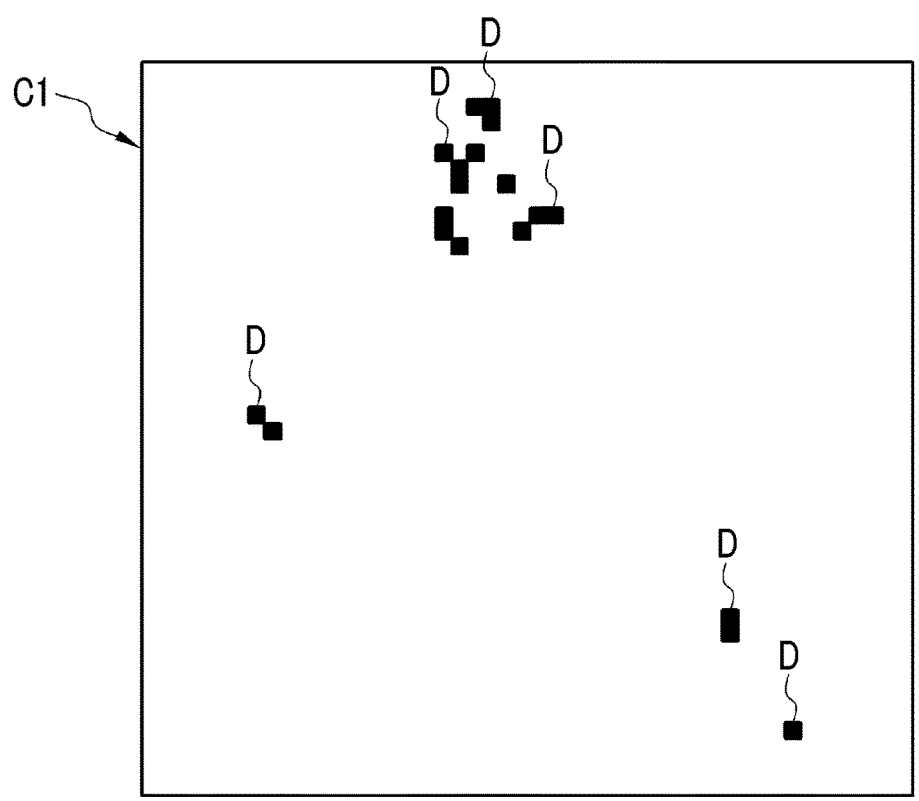

Since the calibration image is an image obtained by emitting X-rays, a defect caused by the defective pixel occurs in the calibration image. In an example of a calibration image C0 in a non-failure state illustrated in FIG. 3A and an example of a calibration image C1 in a failure state illustrated in FIG. 3B, alphabet D indicates a defective pixel. The defective pixel D is a pixel that is not sensitive to incident X-rays and does not generate charge, a pixel that generates change whose amount does not reach a reference range, or a pixel that generates change whose amount is more than the reference range. In the calibration image, a defect appears as a black spot or a white spot. In FIGS. 3A and 3B, the defective pixel D is represented by a black spot. In the calibration image C1 in the failure state illustrated in FIG. 3B, a plurality of defective pixels D occur in adjacent regions and the density of the defective pixels in the entire imaging region is higher than that in the non-failure state. The size of the defect varies depending on the number of defective pixels.

Figure 4:
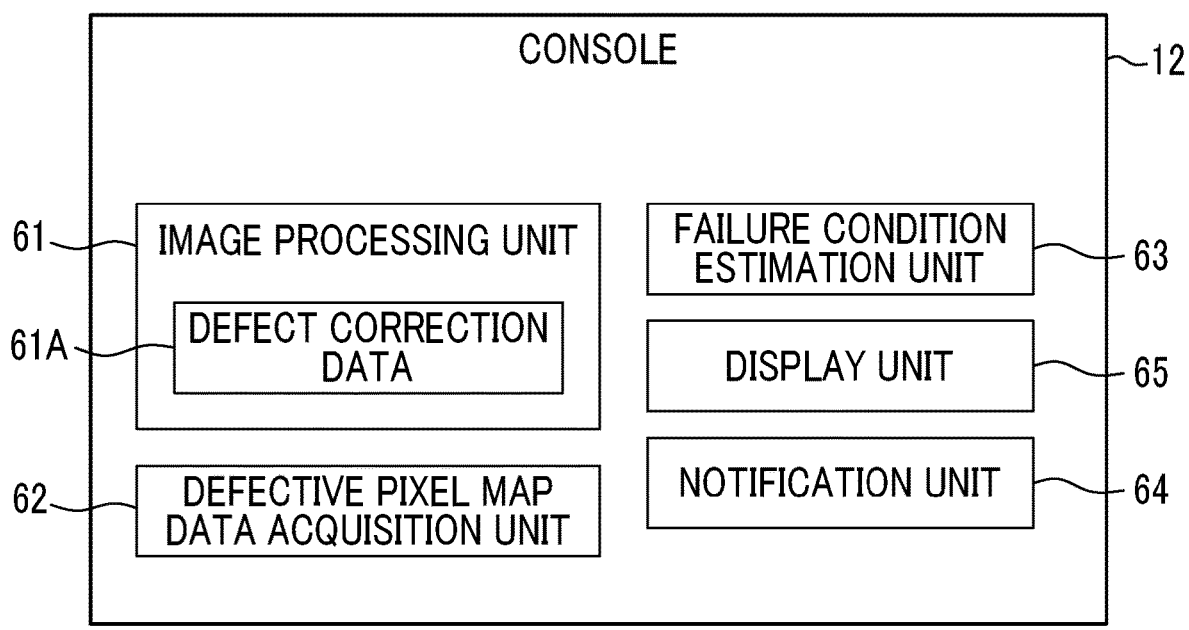
FIG. 4 is a block diagram illustrating the configuration of a console.

The console 12 is a control device that controls the mammography apparatus 10 and an information processing apparatus that processes information using various mammography images. As illustrated in FIG. 4, the console 12 comprises an image processing unit 61, a defective pixel map data acquisition unit 62, a failure condition estimation unit 63, a notification unit 64, and a display unit 65.

The image processing unit 61 performs various kinds of correction for the X-ray image on the basis of, for example, preset correction data. In this embodiment, the image processing unit 61 performs defect correction on the basis of the defect correction data 61A. The display unit 65 displays the X-ray image processed by the image processing unit 61.

The image processing unit 61 creates the defect correction data 61A on the basis of the calibration image acquired during the defect correction calibration of the conversion panel 42. The defect correction data 61A is data for correcting abnormal data which is generated in the X-ray image due to the defective pixel among the pixels 49 of the conversion panel 42. The X-ray image in which abnormal data has been corrected is obtained by defect correction using the defect correction data 61A. Specifically, the defect correction is performed by interpolation based on the data of normal pixels around the defective pixel.

In this embodiment, the calibration image is used to create the defect correction data 61A in the image processing unit 61 and is used as the defective pixel map data in the failure condition estimation unit 63.

During the periodic maintenance, the defective pixel map data acquisition unit 62 controls the X-ray generation unit 32 and the imaging table 33 (FPD 41) to acquire the calibration image (defective pixel map data).

The failure condition estimation unit 63 receives the defective pixel map data acquired by the defective pixel map data acquisition unit 62 and estimates the failure probability of the FPD 41 and the usage state of the FPD 41 at the time of failure.

Figure 5:
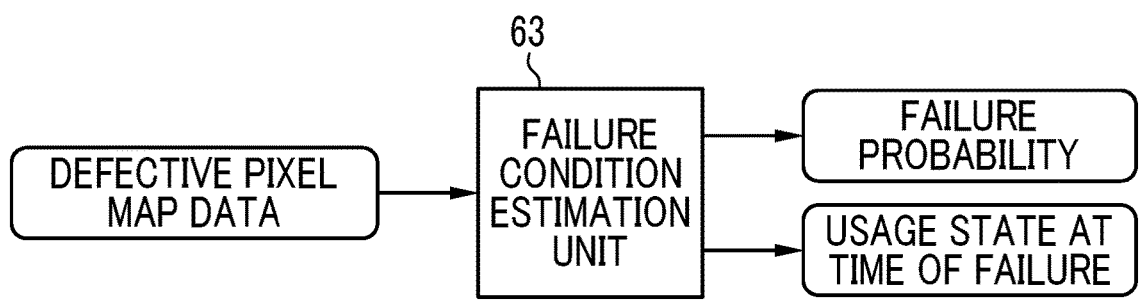
FIG. 5 is a diagram illustrating a failure condition estimation unit.

For example, as illustrated in FIG. 5, the failure condition estimation unit 63 may be configured by a learned model (a so-called artificial intelligence (AI) program) that receives the defective pixel map data and outputs the failure probability or the usage state at the time of failure which is estimated in a case in which the subsequent imaging is performed using the FPD 41.

The failure probability is the probability that the FPD 41 will be out of order within a preset time. The usage state at the time of failure is the time until the FPD 41 is out of order, the number of images captured until the FPD 41 is out of order, or the number of times a high voltage is applied to the FPD 41 until the FPD 41 is out of order. In addition, the radiography unit that detects radiation using an X-ray conversion film, such as an FPD, needs to apply a high voltage of several kilovolts (kV) (2 kV in the case of the FPD) in order to form an electric field for moving electrons and holes generated by the incidence of radiation in a case in which the apparatus starts up and during periodic maintenance. Here, in the radiography unit, the state of the defect changes with the lapse of time since the application of the high voltage. That is, as the number of times the high voltage is applied becomes larger, the probability of failure becomes higher and the state of the apparatus becomes closer to a failure state.

For example, the failure condition estimation unit 63 uses learning data, in which the defective pixel map data actually acquired from the FPD 41 in the failure state is associated with the actual failure probability (100%), the time until the FPD 41 is out of order (0 hours), the number of images (0 images) captured until the FPD 41 is out of order, or the number of times the high voltage is applied to the FPD 41 until the FPD 41 is out of order, for machine learning.

In addition, as the learning data, learning data may be used in which the defective pixel map data acquired from the FPD 41 in the non-failure state (X-ray imaging is not used) is associated with the failure probability, the time until the FPD 41 is out of order, the number of images captured until the FPD 41 is out of order, or the number of times the high voltage is applied to the FPD 41 until the FPD 41 is out of order. In this case, the product design value of the FPD 41 may be used as the value of the failure probability, the time until the FPD 41 is out of order, the number of images captured until the FPD 41 is out of order, or the number of times the high voltage is applied to the FPD 41 until the FPD 41 is out of order.

The failure condition estimation unit 63 acquires evaluation values related to the defect from the defective pixel map data. Specifically, the failure condition estimation unit 63 acquires feature amounts, such as the position of the defective pixels, the density of the defective pixels, the number of defective pixels, and a defect size, as the evaluation values from the defective pixel map data. In this case, the learned model is a learned model that has learned the relationship between the evaluation value and the failure probability or the usage state at the time of failure.

The notification unit 64 sets a threshold value corresponding to the failure probability or the usage state at the time of failure estimated by the failure condition estimation unit 63. In a case in which the value estimated by the failure condition estimation unit 63 or the actual usage state for the estimation value is greater than the threshold value, the notification unit 64 performs notification. As the threshold value set by the notification unit 64, for example, the failure probability estimated by the failure condition estimation unit 63 is equal to or greater than 80%, the actual number of imaging operations with respect to the number of imaging operations until the failure estimated by the failure condition estimation unit 63 is equal to or greater than 80%, or the actual number of times the high voltage is applied with respect to the number of times the high voltage is applied until the failure estimated by the failure condition estimation unit 63 is equal to or greater than 80%. In addition, for example, the user can set the threshold value used in the notification unit 64 to any value using the input unit of the console 12.

For example, the notification unit 64 generates a notification sound as the notification performed in a case in which the above-mentioned value is greater than the threshold value. Alternatively, the notification unit 64 displays information related to the failure of the FPD 41 as the notification. For example, the notification unit 64 displays information indicating that the failure probability is high or the failure time is near on the display unit 65.

Figure 6:
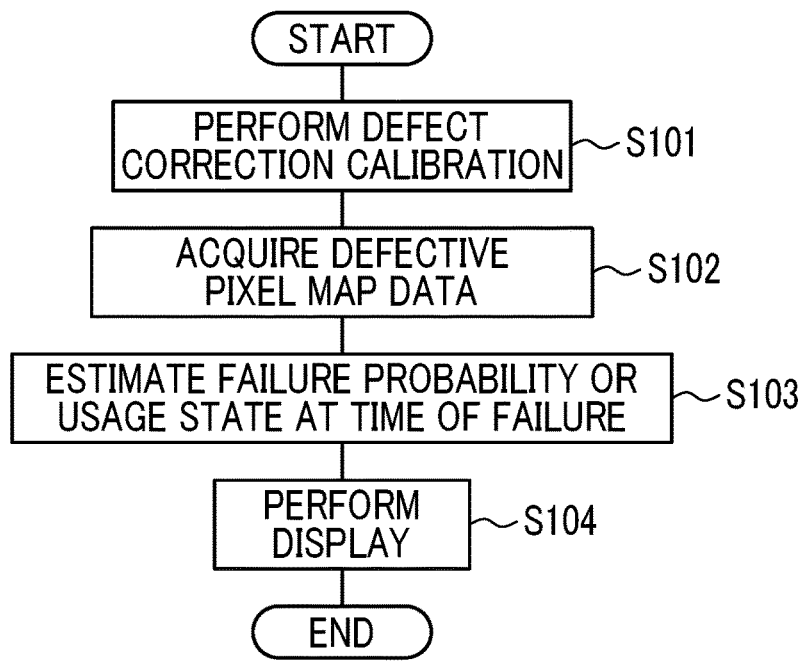
FIG. 6 is a flowchart illustrating the operation of the mammography apparatus.

Next, the operation of the mammography apparatus 10 having the above-mentioned configuration will be described. As illustrated in FIG. 6, for example, during the periodic maintenance, in a case in which defect correction calibration (Step S101), the FPD 41 outputs a calibration image. Then, the defective pixel map data acquisition unit 62 acquires defective pixel map data (Step S102).

In a case in which the defect correction calibration ends and the result of the periodic maintenance is displayed or the content of an imaging request received by the console 12 is displayed, the failure condition estimation unit 63 automatically estimates the failure probability or the usage state at the time of failure using the defective pixel map data (Step S103) and the display unit 65 displays the failure probability or the usage state at the time of failure (Step S104). In a case in which the value acquired by the failure condition estimation unit 63 or the actual usage state with respect to the estimation value is greater than the threshold value, notification is performed.

As described above, in a case in which the defective pixel map data has been acquired, the console 12 estimates and displays the failure probability or the usage state at the time of failure. Since the estimation is performed using the learning model obtained by performing learning on the basis of the defective pixel map data and the usage state of the FPD 41, it is possible to predict the failure of the FPD 41 with high accuracy. In particular, in a case in which the evaluation values, such as the position of the defective pixels, the density of the defective pixels, the number of defective pixels, and a defect size, are acquired from the defective pixel map data and the relationship between the evaluation values and the failure probability or the usage state at the time of failure is learned, it is possible to predict the failure of the FPD 41 with higher accuracy.

In the above-described embodiment, during the periodic maintenance, the defect correction calibration is performed to acquire the defective pixel map data in response to a command from the console 12 and the failure probability or the usage state at the time of failure is estimated. However, the invention is not limited thereto. During remote maintenance, the failure condition estimation unit 63 may estimate the failure probability or the usage state at the time of failure. In this case, the defect correction calibration may be automatically performed at a preset time to acquire the defective pixel map data and the estimation result of the failure probability or the usage state at the time of the failure may be transmitted to, for example, an information processing apparatus that is installed in a remote place and is connected to the console 12 wirelessly or in a wired manner.

In the above-described embodiment, the failure condition estimation unit 63 is an AI program. However, the failure condition estimation unit 63 may not be the AI program, but may be configured to include the AI program. For example, the failure condition estimation unit 63 can estimate the failure probability or the usage state at the time of failure, using the learned model that outputs the failure probability or the usage state at the time of failure in response to the input of the defective pixel map data. Therefore, in the mammography apparatus 10, for example, the failure condition estimation unit 63 can communicate with an information processing apparatus or an analysis apparatus provided with the learned model that operates in an apparatus other than the console 12 and can estimate the failure probability or the usage state at the time of failure using the learned model. In addition, since an AI program is included, a case in which the failure condition estimation unit 63 is an AI program is an aspect of the case in which the failure condition estimation unit 63 includes an AI program. In a case in which the failure condition estimation unit 63 is an AI program and in a case in which the failure condition estimation unit 63 includes an AI program, the accuracy of determination is particularly high.

Figure 7:
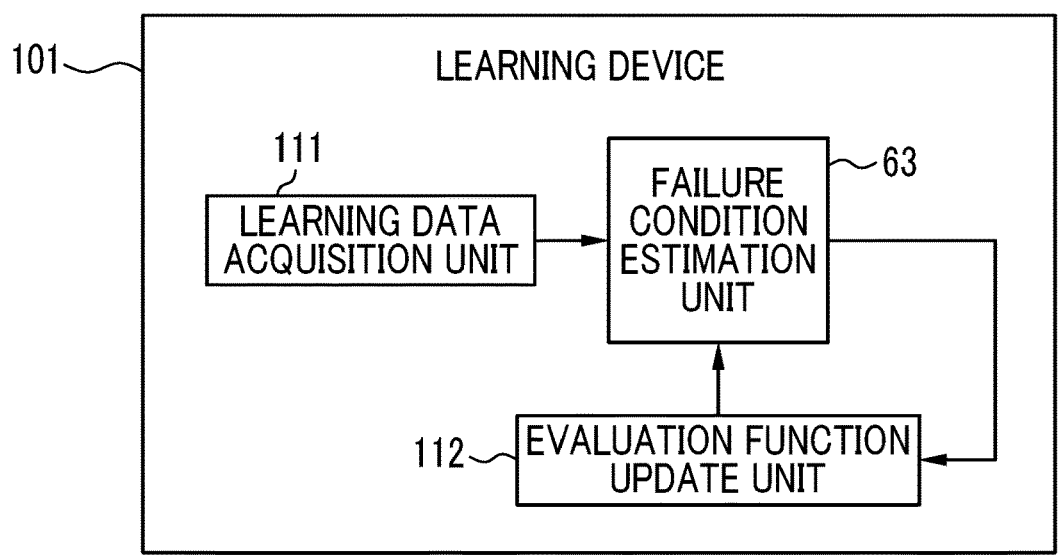
FIG. 7 is a block diagram illustrating a learning device that trains the failure condition estimation unit.

The failure condition estimation unit 63 which is an AI program can be trained using a learning device 101 illustrated in FIG. 7. The learning device 101 is a device for training (optimizing) the failure condition estimation unit 63 and comprises a learning data acquisition unit 111 and an evaluation function update unit 112.

The learning data acquisition unit 111 acquires data used to train the failure condition estimation unit 63 (learning unit). Specifically, the learning data acquisition unit 111 acquires learning data in which the defective pixel map data is associated with a recording value of the failure probability of the FPD 41 or the usage state at the time of failure as described in the above-mentioned embodiment. Then, the learning data acquisition unit 111 inputs the defective pixel map data as an explanatory variable and the recording value of the failure probability of the FPD 41 or the usage state at the time of failure as a correct answer label to the failure condition estimation unit 63 to be trained.

The failure condition estimation unit 63 calculates an estimation value (so-called evaluation value) of an objective variable, using the defective pixel map data as the explanatory variable and an evaluation model (for example, an evaluation function used in a specific regression analysis model) that obtains the objective variable from the explanatory variable, and outputs an error between the estimation value of the objective variable and the correct answer label. In this learning, the objective variable is the range of the failure probability of the FPD 41 or the usage state at the time of failure.

The evaluation function update unit 112 optimizes the values of parameters used by the failure condition estimation unit 63 in the evaluation model, using the error between the estimation value of the objective variable and the correct answer label output from the failure condition estimation unit 63 that is performing learning. The optimization means an operation that calculates parameters for minimizing the error for a plurality of sets of the explanatory variables and the correct answer labels and updates the parameters used in the evaluation model to the calculated parameters. The failure condition estimation unit 63 becomes an optimized evaluation model (learned model) by the repetition of the above-mentioned learning by the learning device 101.

The learning device 101 is a device that performs so-called supervised learning. However, the learning device 101 can train the failure condition estimation unit 63 using unsupervised learning or reinforcement learning. In addition, the evaluation model and the optimization method may be changed according to a specific learning aspect. Further, the failure condition estimation unit 63 may be optimized by supervised learning using an explanatory variable, an objective variable, and/or an evaluation model different from those in the learning device 101.

The reinforcement learning is a method which sets a state, an action, and an evaluation value according to the environment and calculates the action of optimizing the cumulative sum of the evaluation values in all of the set states and is applied to a technique such as obstacle avoidance. In a case in which the reinforcement learning is applied to the learning device 101, first, feature amounts are extracted on the basis of the learning data acquired by the learning data acquisition unit 111. The feature amounts may be feature amounts that can be extracted from learning data other than the position of the defective pixels, the density of the defective pixels, the defect size described in the above-mentioned embodiment. For example, an imaging interval and the frequency of imaging until the defective pixel map data is acquired may be extracted as the feature amounts. The failure condition estimation unit 63 as a learning unit calculates a new evaluation model on the basis of the extracted feature amounts and updates the evaluation model to the new evaluation model.

In the learning data used for learning in the embodiment and the modification examples, the above-mentioned defective pixel map data, the recording value of the failure probability of the FPD 41 or the usage state at the time of failure, and any one of the number of images captured until the FPD 41 is out of order after the acquisition of the defective pixel map data, the time until the FPD 41 is out of order after the acquisition of the defective pixel map data, or the imaging frequency of the FPD 41 per predetermined time may be associated with each other.

For example, in the embodiment and the modification examples, the console 12 functions as the information processing apparatus. However, another information processing apparatus (for example, a computer functioning as the analysis apparatus) which is operatively associated with the console 12 may have the functions of the console 12 as the information processing apparatus. For example, in each of the embodiment and the modification examples, the apparatus main body 11 may have the functions of the console 12 as the information processing apparatus. For example, in each of the embodiments and the modification examples, in a case in which the console 12 or the apparatus main body 11 has the functions of the console 12 as the information processing apparatus, the entire mammography apparatus 10 functions as the information processing apparatus. In addition, for example, in each of the embodiments and the modification examples, the functions of the console 12 as the information processing apparatus may be dispersed to a plurality of apparatuses (for example, a plurality of computers).

For example, in the above-described embodiments, the following various processors can be used as the hardware structure of processing units performing various processes, such as the image processing unit 61, the defective pixel map data acquisition unit 62, the failure condition estimation unit 63, the learning data acquisition unit 111, and the evaluation function update unit 112. The various processors include a CPU which is a general-purpose processor executing software (program) to function as various processing units, a graphical processing unit (GPU), a programmable logic device (PLD), such as a field programmable gate array (FPGA), which is a processor whose circuit configuration can be changed after manufacture, and a dedicated electric circuit which is a processor having a dedicated circuit configuration designed to perform various processes.

One processing unit may be configured by one of the various processors or a combination of two or more processors of the same type or different types (for example, a combination of a plurality of FPGAs and a combination of a CPU and an FPGA). In addition, a plurality of processing units may be configured by one processor. A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

EXPLANATION OF REFERENCES

- 10: mammography apparatus
- 11: apparatus main body
- 12: console
- 31: support
- 32: X-ray generation unit
- 33: imaging table
- 34a: gripping portion
- 34b: gripping portion
- 36: compression plate
- 37: elevating unit
- 40: movable unit
- 41: FPD
- 42: conversion panel
- 43: scanning driving unit
- 44: reading unit
- 45: FPD control unit
- 46: analog/digital (A/D) converter
- 47: memory
- 48: communication unit
- 49: pixel
- 50: imaging region
- 51: thin film transistor (TFT)
- 52: pixel electrode
- 53: scanning line
- 54: signal line
- 61: image processing unit
- 61A: defect correction data
- 62: defective pixel map data acquisition unit
- 63: failure condition estimation unit
- 64: notification unit
- 65: display unit
- 101: learning device
- 111: learning data acquisition unit
- 112: evaluation function update unit
- C0: calibration image
- C1: calibration image
- D: defective pixel

What is claimed is:

1. An information processing apparatus comprising:
a processor configured to:
   acquire defective pixel map data indicating positional information of a defective pixel which is defective among a plurality of pixels forming a radiography unit; and
   estimate a failure probability of the radiography unit or a usage state of the radiography unit at the time of failure, using a learned model that receives the defective pixel map data and outputs the failure probability of the radiography unit or the usage state of the radiography unit at the time of failure.

2. The information processing apparatus according to claim 1,
wherein the processor sets a threshold value corresponding to the failure probability or the usage state at the time of failure and performs notification in a case in which the failure probability or the usage state at the time of failure is greater than the threshold value.

3. The information processing apparatus according to claim 1,
wherein the processor acquires a calibration image output from the radiography unit as the defective pixel map data.

4. The information processing apparatus according to claim 1,
wherein the failure probability is a probability that the radiography unit will be out of order within a preset time.

5. The information processing apparatus according to claim 1,
wherein the usage state at the time of failure is a time until the radiography unit is out of order, the number of images captured until the radiography unit is out of order, or the number of times a high voltage is applied to the radiography unit until the radiography unit is out of order.

6. A learning device comprising:
a processor configured to:
   acquire learning data in which defective pixel map data indicating positional information of a defective pixel which is defective among a plurality of pixels forming a radiography unit is associated with a recording value of a failure probability of the radiography unit or a usage state of the radiography unit at the time of failure;
   calculate an evaluation value of the failure probability or the usage state at the time of failure from the defective pixel map data using an evaluation function; and
   update the evaluation function, using an error between the evaluation value of the failure probability or the usage state at the time of failure calculated by the learning unit using the evaluation function and the recording value of the failure probability or the usage state at the time of failure in the learning data, in a case in which the learning data is acquired,
wherein the processor uses the updated evaluation function.

7. The learning device according to claim 6,
wherein the failure probability is a probability that the radiography unit will be out of order within a preset time.

8. The learning device according to claim 6,
wherein the usage state at the time of failure is the number of images captured until the radiography unit is out of order after the use of the radiography unit starts or the number of times a high voltage is applied to the radiography unit until the radiography unit is out of order.

9. The learning device according to claim 6,
wherein, in the learning data, any one of the number of images captured until the radiography unit is out of order after the defective pixel map data is acquired, a time until the radiography unit is out of order after the defective pixel map data is acquired, or an imaging frequency of the radiography unit per predetermined time, the defective pixel map data, and the recording value of the failure probability of the radiography unit or the usage state of the radiography unit at the time of failure are associated with each other.

10. A non-transitory device-readable medium for storing a device-executable program that drives an information processing apparatus comprising a processor that acquires defective pixel map data indicating positional information of a defective pixel which is defective among a plurality of pixels forming a radiography unit, the device-executable program causing the information processing apparatus to perform:

estimating a failure probability of the radiography unit or a usage state of the radiography unit at the time of failure, using a learned model that receives the defective pixel map data and outputs the failure probability of the radiography unit or the usage state of the radiography unit at the time of failure.

* * * * *